(12) United States Patent
Roshanali et al.

(10) Patent No.: US 9,480,469 B2
(45) Date of Patent: Nov. 1, 2016

(54) SURGICAL DEVICE FOR CLOSURE OF ATRIAL SEPTAL DEFECT WITH MINIMALLY INVASIVE APPROACH

(71) Applicants: Farideh Roshanali, Tehran (IR); Seyed Nasser Pourmoosavi, Tehran (IR); Ali Namazi, Tehran (IR)

(72) Inventors: Farideh Roshanali, Tehran (IR); Seyed Nasser Pourmoosavi, Tehran (IR); Ali Namazi, Tehran (IR)

( * ) Notice: Subject to any disclaimer, the term of this patent is extended or adjusted under 35 U.S.C. 154(b) by 0 days.

(21) Appl. No.: 14/947,598

(22) Filed: Nov. 20, 2015

(65) Prior Publication Data

US 2016/0074026 A1 Mar. 17, 2016

Related U.S. Application Data

(60) Continuation of application No. 13/835,587, filed on Mar. 15, 2013, now Pat. No. 9,192,365, which is a division of application No. 12/654,978, filed on Jan. 12, 2010, now Pat. No. 8,398,658.

(60) Provisional application No. 61/154,388, filed on Feb. 21, 2009.

(51) Int. Cl.
*A61B 17/04* (2006.01)
*A61B 17/00* (2006.01)

(52) U.S. Cl.
CPC ....... *A61B 17/0057* (2013.01); *A61B 17/0469* (2013.01); *A61B 17/0482* (2013.01); *A61B 2017/00597* (2013.01); *A61B 2017/00615* (2013.01); *A61B 2017/00946* (2013.01); *A61B 2034/2063* (2016.02)

(58) Field of Classification Search
CPC .......... A61B 17/0057; A61B 17/0469; A61B 17/0482; A61B 17/083; A61B 17/08; A61B 17/28; A61B 17/29; A61B 17/0487; A61B 17/128; A61B 17/1285; A61B 17/068; A61B 17/0682; A61B 17/0684; A61B 17/0686
USPC ............... 606/151, 198, 139–150; 623/23.72
See application file for complete search history.

(56) References Cited

U.S. PATENT DOCUMENTS

| | | |
|---|---|---|
| 1,822,330 A | 9/1931 | Ainslie |
| 4,523,592 A | 6/1985 | Daniel |
| 4,605,002 A | 8/1986 | Rebuffat |

(Continued)

OTHER PUBLICATIONS

Notice of Allowance dated Nov. 26, 2012 in U.S. Appl. No. 12/654,978.

(Continued)

*Primary Examiner* — Melanie Tyson
*Assistant Examiner* — Erich Herbermann
(74) *Attorney, Agent, or Firm* — Farhad Shir

(57) ABSTRACT

A method of providing a surgical device for closure of Atrial Septal Defect (ASD) with minimally invasive approach includes a head portion that includes a distal jaw being distal relative to a person holding the surgical device, a guide rod which drives the distal jaw, and a plurality of first suture-guide channels attached to the distal jaw, and a body portion which is stationary and includes a cylindrical base, a proximal jaw attached to the cylindrical base, and a plurality of second suture-guide channels attached to the proximal jaw. A lever drives the distal jaw away from the proximal jaw such that the distal jaw and the proximal jaw are spaced on different sides of an ASD hole. After a suture thread sutures a pericardium patch, the lever pulls the distal jaw backward toward the proximal jaw such that the first suture-guide channels couple with the second suture-guide channels.

11 Claims, 6 Drawing Sheets

(56) References Cited

U.S. PATENT DOCUMENTS

| | | | |
|---|---|---|---|
| 5,152,769 A | 10/1992 | Baber | |
| 5,250,058 A | 10/1993 | Miller et al. | |
| 5,356,424 A | 10/1994 | Buzerzk et al. | |
| 5,364,408 A | 11/1994 | Gordon | |
| 5,374,275 A * | 12/1994 | Bradley | A61B 17/0469 606/139 |
| 5,382,258 A | 1/1995 | Chow | |
| 5,387,221 A | 2/1995 | Bisgaard | |
| 5,843,098 A | 12/1998 | Allen et al. | |
| 5,891,159 A | 4/1999 | Sherman et al. | |
| 6,048,351 A | 4/2000 | Gordon et al. | |
| 6,071,289 A | 6/2000 | Stefanchik et al. | |
| 6,290,674 B1 | 9/2001 | Roue et al. | |
| 6,464,707 B1 | 10/2002 | Bjerken | |
| 6,503,259 B2 | 1/2003 | Huxel et al. | |
| 2002/0026159 A1 * | 2/2002 | Zhu | A61B 17/0057 604/289 |
| 2002/0100485 A1 | 8/2002 | Stevens et al. | |
| 2003/0083674 A1 | 5/2003 | Gibbens, III | |
| 2004/0186486 A1 * | 9/2004 | Roue | A61B 17/00234 606/139 |
| 2005/0015101 A1 | 1/2005 | Gibbens et al. | |
| 2005/0043747 A1 | 2/2005 | Field et al. | |
| 2005/0216038 A1 | 9/2005 | Meade et al. | |
| 2006/0069397 A1 * | 3/2006 | Nobles | A61B 17/0057 606/144 |
| 2006/0095052 A1 * | 5/2006 | Chambers | A61B 17/0057 606/139 |
| 2006/0190016 A1 | 8/2006 | Onuki et al. | |
| 2006/0282096 A1 | 12/2006 | Papa et al. | |
| 2008/0086075 A1 * | 4/2008 | Isik | A61B 17/3423 604/27 |
| 2009/0138029 A1 | 5/2009 | Saliman et al. | |

OTHER PUBLICATIONS

Office Action dated Aug. 15, 2012 in U.S. Appl. No. 12/654,978.
Notice of Allowance dated Jul. 27, 2015 in U.S. Appl. No. 13/35,587.

* cited by examiner

SURGICAL DEVICE FOR CLOSURE OF ATRIAL SEPTAL DEFECT WITH MINIMALLY INVASIVE APPROACH

CROSS REFERENCE TO RELATED APPLICATIONS

The present Application is a Continuation Application of U.S. application Ser. No. 13/835,587, filed on Mar. 15, 2013, which is a Divisional Application of U.S. application Ser. No. 12/654,978, filed on Jan. 12, 2010, now U.S. Pat. No. 8,398,658, which benefits a priority from U.S. Provisional Patent Application No. 61/154,388, filed on Feb. 21, 2009, the entire contents of which are incorporated herein by reference.

BACKGROUND OF THE INVENTION

1. Field of the Invention

The present invention relates to a method for providing a minimally invasive closure of atrial septal defect without cardiopulmonary bypass and, in particular, a device and a method for minimally invasive closure of atrial septal defect via a right minithoracotomy to deploy a pericardial patch under a transesophageal echocardiography guidance.

2. Description of the Related Art

There are currently two methods for the closure of atrial septal defect (ASD), conventional or minimally invasive surgical method and percutaneous device transcatheter closure. The former requires cardiopulmonary bypass (CPB), and the latter, which entails the deployment of a sizable device in the heart, is hampered by the defect size and circumferential margins adjacent to the superior and inferior venae cavae, pulmonary vein, mitral valve, and aortic sinus.

Recently, robotically assisted surgical systems have enhanced the precision of minimally invasive cardiac surgery. These costly procedures, however, still require the CPB. CPB is widely recognized as having a number of adverse effects, including generation of microemboli and an inflammatory response associated with increased cytokine production and complement activation, begetting neurological dysfunction in adults and neurodevelopmental dysfunction especially in children.

In addition, recently cosmetic sequelae following cardiac surgery has rendered minimal access approaches with equivalent results and a nearly invisible scar is more favorable.

SUMMARY OF THE INVENTION

In view of the foregoing and other exemplary problems, disadvantages, and drawbacks of the aforementioned devices and methods, it is an exemplary purpose of the present invention to provide a device and a method for minimally invasive closure of atrial septal defect without cardiopulmonary bypass.

The present invention includes a surgical device and method for closure atrial septal defect with minimally invasive approach. The device includes a head portion which is movable and includes a distal jaw placed distal relative to a person holding the surgical device, a guide rod which drives the distal jaw, and a plurality of first suture-guide channels attached to the distal jaw, and a body portion which is stationary and includes a cylindrical base, a proximal jaw attached to the cylindrical base, and a plurality of second suture-guide channels attached to the proximal jaw.

The guide rod drives the distal jaw to pass a pericardium patch through a patient's ASD while the proximal end remains extracorporeal. The first suture-guide channels and the second suture-guide channels guide a suture thread to suture the pericardium patch onto an ASD rim.

The head portion may include four first suture-guide channels, and the body portion may include four second suture-guide channels.

Further, each of the first suture-guide channels includes an arm which connects a center portion of each of the first suture-guide channels to the distal jaw. Each of the first suture-guide channels may be spaced apart from an adjacent one of the first suture-guide channels such that the arm of the each of the first suture-guide channels is oriented at 90 degrees with respect to an arm of the adjacent one of the first suture-guide channels.

Also, each of the second suture-guide channels includes an arm which connects a center portion of each of the second suture-guide channels to the proximal jaw. Each of the second suture-guide channels may be spaced apart from an adjacent one of the second suture-guide channels such that the arm of the each of the second suture-guide channels is oriented at 90 degrees with respect to an arm of the adjacent one of the second suture-guide channels. The first suture-guide channels may be oriented at 90 degrees to the second suture-guide channels such that the first suture-guide channels couple with the second suture-guide channels to form a circle.

In the surgical device, the first suture-guide channels are attached to a plurality of first arms, each of the first anus connects a center portion of each of the first suture-guide channels to the distal jaw. The first arms may be oriented at 0, 90, 180, and 270 degrees with respect to a center of the guide rod.

Further, the second suture-guide channels are attached to a plurality of second arms, each of the second arms connects a center portion of each of the second suture-guide channels to the proximal jaw. The second arms may be oriented at 45, 135, 225, and 315 degrees with respect to the center of the guide rod.

In the surgical device, the pericardial patch is connected to a suction device via a flexible pipe. Also, a threading thread attaches the pericardial patch to the distal jaw, in which ends of the threading thread are extracorporeal.

Further, a lever drives the distal jaw away from the proximal jaw such that the distal jaw and the proximal jaw are spaced on different sides of an ASD hole. After the suture thread sutures the pericardium patch, the lever pulls the distal jaw backward toward the proximal jaw such that the first suture-guide channels couple with the second suture-guide channels to form a circle.

The lever may include a wire and a spring or a crown wheel and a pinion. The level drives the distal jaw by pulling the wire.

In the surgical device, the first suture-guide channels and the second suture-guide channels guide a needle that carries the suture thread to suture the pericardium patch onto the ASD rim. The needle includes a long malleable needle, and passes the suture thread through a space between the guide rod and an internal section of the cylindrical base. The pericardium patch may be glued to the distal jaw.

Another aspect of the present invention includes a method of providing a surgical device for closure of atrial septal defect with minimally invasive approach.

The method includes drawing a pericardial patch over a distal jaw of the surgical device, while keeping a first suture-guide channels attached to the distal jaw and a second suture-guide channels attached to a proximal jaw of the surgical device closed, inserting the surgical device through a hole incised in an intercostal space of a patient and drawing the surgical device toward the ASD, while keeping the proximal end of the surgical device extracorporeal, manipulating forward a guide rod of the surgical device to drive the distal jaw to negotiate the distal jaw through the ASD, opening the first suture-guide channels and the second suture-guide channels to position the first suture-guide channels and the second suture-guide channels around the ASD, withdrawing the distal jaw such that the distal jaw latches onto the proximal jaw, pulling back the pericardial patch in conjunction with an ASD rim to secure the pericardial patch and the ASD rim between the first suture-guide channels and the second suture-guide channels, employing a long malleable needle extracorporeally to pass a suture thread into a space between the guide rod and an internal part of a cylindrical base, which supports a body portion of the surgical device, to suture the pericardial patch onto the ASD rim through the first suture-guide channels and the second suture-guide channels, re-steering forward the distal jaw to release the pericardial patch and to suture the pericardial patch onto the ASD rim, shutting the first suture-guide channels and the second suture-guide channels into respective original positions on the distal jaw and the proximal jaw, withdrawing the distal jaw from the ASD and lodging the distal jaw upon the proximal jaw, removing the surgical device from a body of the patient, and orienting a plurality of knots extracorporeally toward the ASD to complement the suture of the pericardial patch.

The first suture-guide channels may be attached to a plurality of first arms, each of the first arms connects a center portion of each of the first suture-guide channels to the distal jaw. The first arms may be oriented at 0, 90, 180, and 270 degrees with respect to a center of the guide rod. The second suture-guide channels may be attached to a plurality of second arms. Each of the second arms connects a center portion of each of the second suture-guide channels to the proximal jaw. The second arms may be oriented at 45, 135, 225, and 315 degrees with respect to the center of the guide rod.

In the method, after the suture thread sutures the pericardium patch, a lever pulls the distal jaw backward toward the proximal jaw such that the first suture-guide channels couple with the second suture-guide channels to form a circle.

Further, each of the first suture-guide channels includes an arm which connects a center portion of each of the first suture-guide channels to the distal jaw. Each of the first suture-guide channels is spaced apart from an adjacent one of the first suture-guide channels such that the arm of the each of the first suture-guide channels may be oriented at 90 degrees with respect to an arm of the adjacent one of the first suture-guide channels. Each of the second suture-guide channels comprises an arm which connects a center portion of each of the second suture-guide channels to the proximal jaw.

Each of the second suture-guide channels is spaced apart from an adjacent one of the second suture-guide channels such that the arm of the each of the second suture-guide channels may be oriented at 90 degrees with respect to an arm of the adjacent one of the second suture-guide channels. The first suture-guide channels may be oriented at 90 degrees to the second suture-guide channels such that the first suture-guide channels couple with the second suture-guide channels to form a circle.

With its unique and novel features, the present invention provides a device and a method for minimally invasive approach for the closure of all forms and sizes of secundum ASD which obviates the need for CPB, radiation, and deployment of an expensive bulky device in the heart. This procedure is carried out via a right minithoracotomy to deploy a pericardial patch under transesophageal echocardiography guidance. The method of the present invention does not require additional work for the closure of more than one defect with aneurismal rims or defects with deficient margins. Further, it offers an added element of safety compared with the transcutaneous route, because the procedure is performed in an operating room with CPB facilities available for any exigencies. This approach also minimizes the risk of atrioventricular valve distortion and obstruction of the superior and inferior venae cavae or coronary sinus.

Other advantages of this technique are reduced associated pain, better cosmetic results, shorter recovery time, and fewer complications.

BRIEF DESCRIPTION OF THE DRAWINGS

The foregoing and other exemplary purposes, aspects and advantages will be better understood from the following detailed description of the exemplary embodiments of the invention with reference to the drawings, in which.

DETAILED DESCRIPTION OF THE EMBODIMENTS OF THE INVENTION

Figure 1:
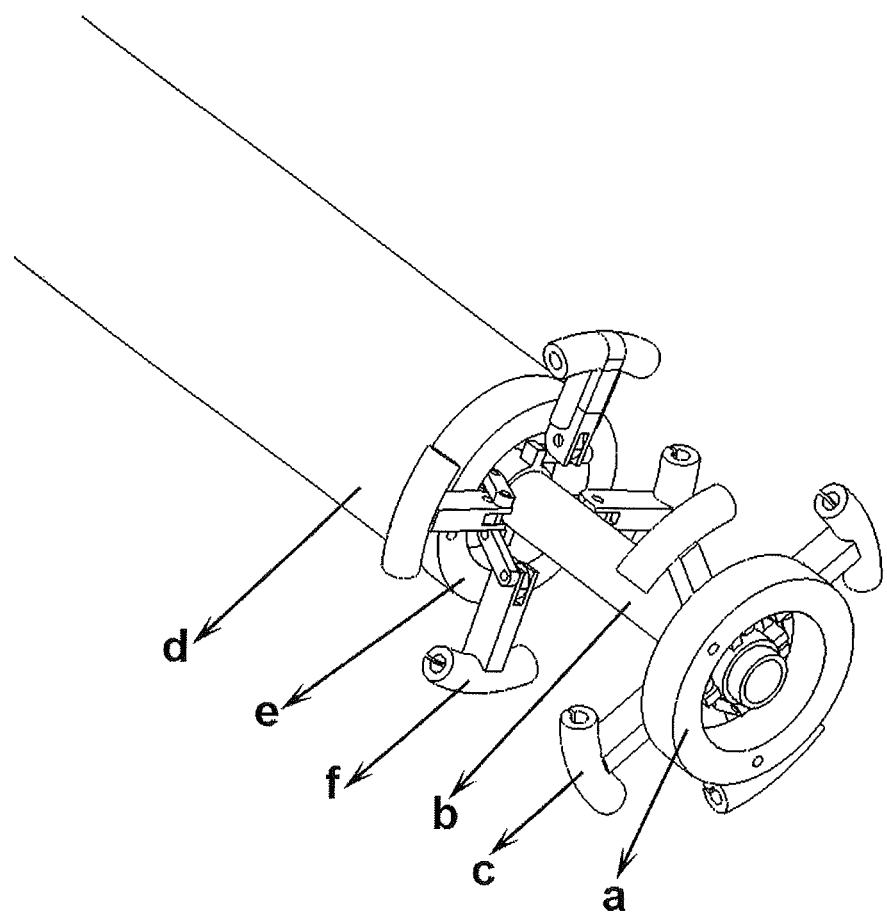
FIG. 1 illustrates an exemplary device for minimally invasive closure of atrial septal defect, in accordance with an exemplary aspect of the present invention.

Referring now to the drawings, FIG. 1 illustrates an exemplary aspect of the present invention. Specifically, FIG. 1 illustrates an exemplary device 100 for minimally invasive closure of atrial septal defect without cardiopulmonary bypass, in accordance with an exemplary aspect of the present invention.

As shown in FIG. 1, the device 100 includes two main parts, a head, which is moveable and includes of a guide rod (b), distal jaw, relative to the person holding the device (a), and 4 suture-guide channels (c), and a body, which is stationary and includes a cylindrical base (d), a proximal jaw (e), relative to the person who holds the device, and 4 suture-guide channels (f). The 8 suture-guide channels (c) and (f), oriented at 90 degrees relative to one another and mounted upon the distal jaw (a) and proximal jaw (e), form a circle, with the channels at the distal jaw (a) being at 0, 90, 180, and 270 degrees and the channels at the proximal jaw (e) being at 45, 135, 225, and 315 degrees such that the channels can slide open and shut radially.

A 3-cm incision is arranged in the right fourth midaxillary intercostal space. The lateral mini thoracotomy exposes the pericardium, which is opened and sutured with five 2-0 stay sutures to suspend the heart. Right atriotomy follows the placement of two parallel 4-0 polypropylene purse string sutures, approximately 10 mm in diameter. The patient is then administered about 1.0 mg/kg of heparin, and the activated clotting time is confirmed to be greater than 250 s.

Figure 2A:
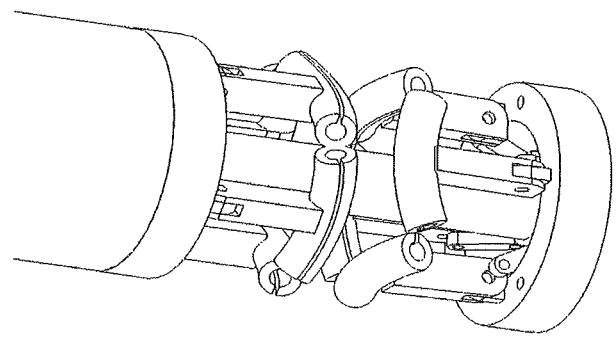
FIG. 2a illustrates a view of the distal jaw while the suture-guide channels remain shut, before drawing a pericardium patch over the device for minimally invasive closure of atrial septal defect, in accordance with an exemplary aspect of the present invention.
Figure 2B:
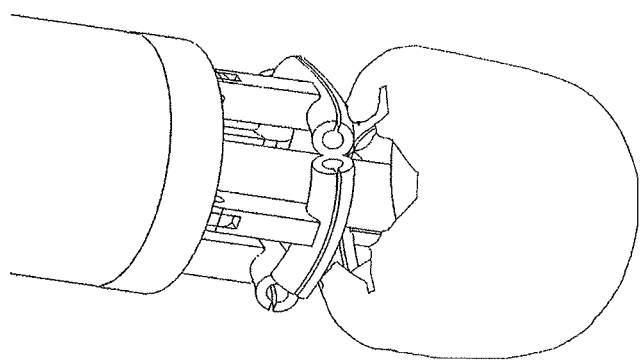
FIG. 2b illustrates a view of the distal jaw while the suture-guide channels remain shut, after drawing a pericardium patch over the device for minimally invasive closure of atrial septal defect, in accordance with an exemplary aspect of the present invention.

A pericardium patch, with the desired size for the closure of ASD, is cut and drawn over the distal jaw (a) while the suture-guide channels (c) and (f) remain shut, as shown in the exemplary FIGS. 2a and 2b.

Figure 3:
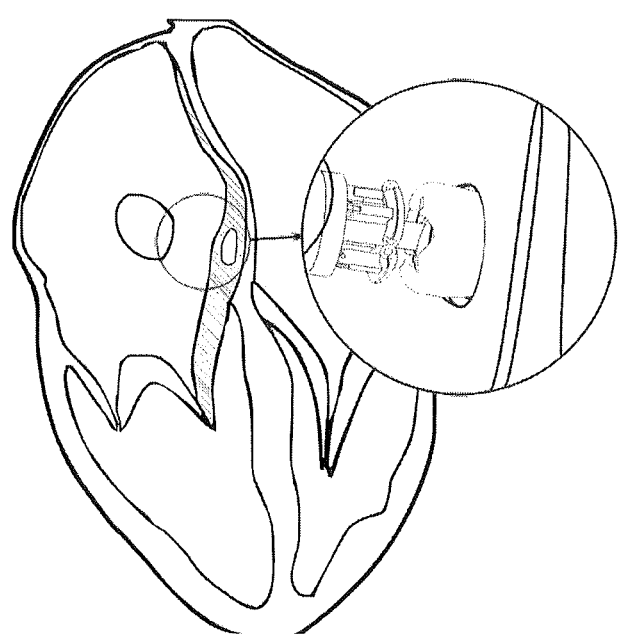
FIG. 3 illustrates a cross section view of heart, the ASD, and the distal jaw of the device while it advanced toward the ASD, in accordance with an exemplary aspect of the present invention.

The device is thereafter inserted through the hole incised in the patient's intercostal space and advanced toward the ASD, while the proximal end of the device body, relative to the person using the device, remains extracorporeal, as illustrated in the exemplary FIG. 3.

The guide rod (b) is manipulated to drive the distal jaw (a) forward and negotiate it through the ASD.

Figure 4:
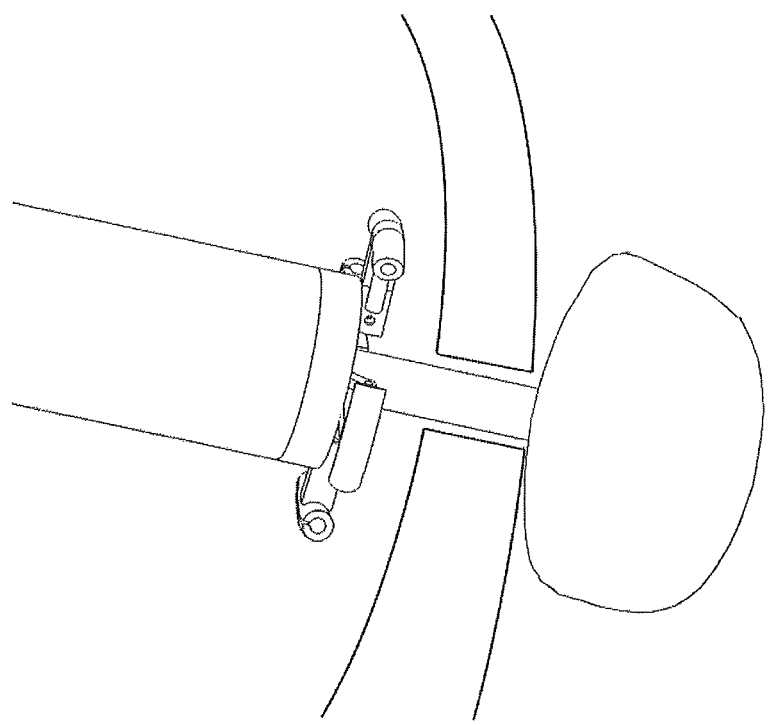
FIG. 4 illustrates a cross sectional view of the ASD while the suture-guide channels are opened and positioned around, in accordance with an exemplary aspect of the present invention.

As shown in the exemplary FIG. 4, in this exemplary aspect, the suture-guide channels (c) and (f) are subsequently opened and positioned around the ASD.

Figure 5A:
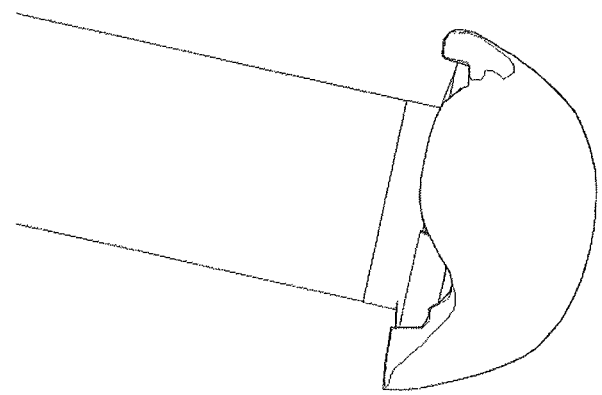
FIG. 5a illustrates a view of the device when the distal jaw is withdrawn and pericardium patch in conjunction with the ASD rim is firmly secured between the suture-guide channels, in accordance with an exemplary aspect of the present invention.
Figure 5B:
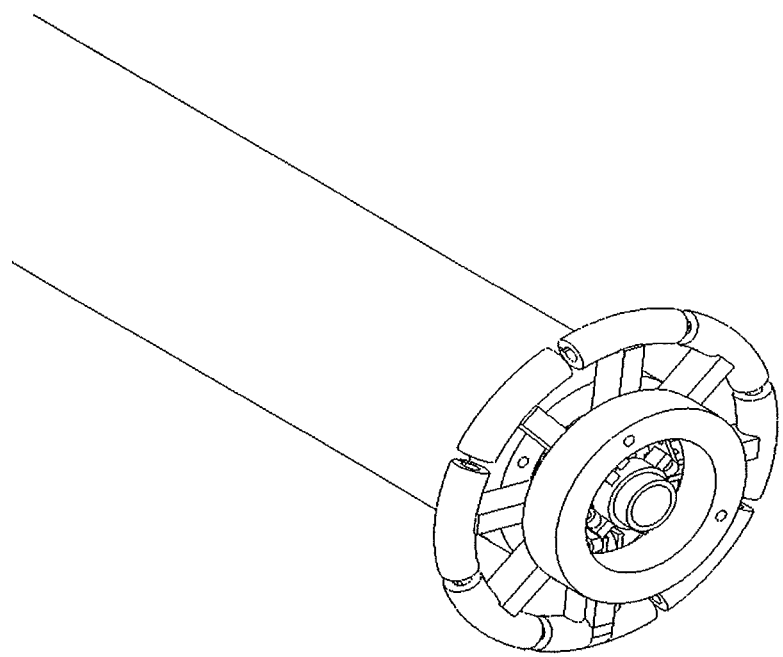
FIG. 5b illustrates a view of the device when the distal jaw is withdrawn and latches onto the proximal jaw, in accordance with an exemplary aspect of the present invention.

The distal jaw (a) is withdrawn so that it latches onto the proximal jaw (e), to pull back the pericardium patch in conjunction with the ASD rim and firmly secure them between the suture-guide channels (c) and (f), as depicted in the exemplary FIGS. 5a and 5b.

A long malleable needle is employed extracorporeally to pass a suture thread into the space between the guide rod (b) and the internal part of the cylindrical base (d) and to suture the pericardium patch onto the ASD rim through the suture-guide channels (c) and (f).

Figure 6:
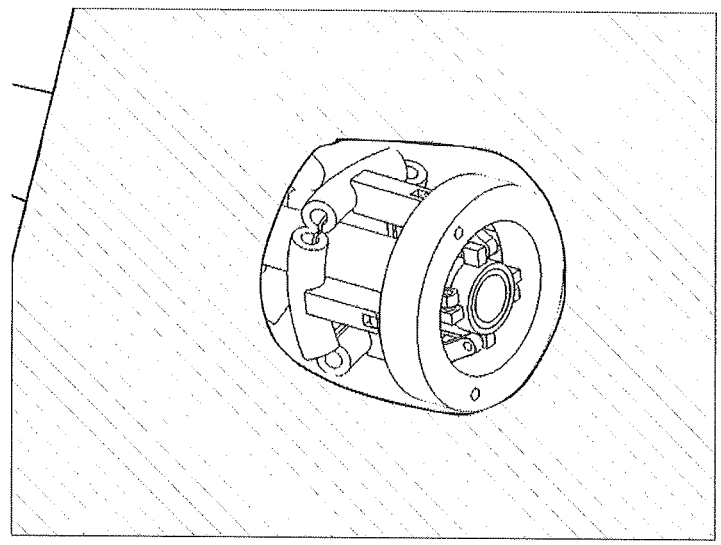
FIG. 6 illustrates a view of the device while the distal jaw is re-steered forward to releases the pericardium patch for snugly suturing onto the ASD rim, in accordance with an exemplary aspect of the present invention.

The distal jaw (a) is re-steered forward so that it releases the pericardium patch, which is snugly sutured onto the ASD rim, as illustrated in the exemplary FIG. 6.

Figure 7:
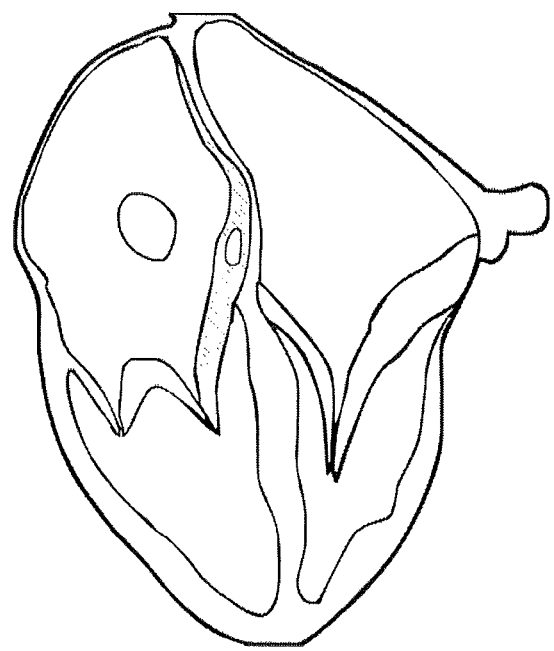
FIG. 7 illustrates cross section view of the heart after closure of the ASD, in accordance with an exemplary aspect of the present invention.

The suture-guide channels (c) and (f) are shut and retracted to their respective original positions on the jaws. The distal jaw (a) is afterward withdrawn through the ASD and is lodged upon the proximal jaw (e), as shown in the exemplary FIG. 7.

Then, the device is extracted from the patient's body. Finally, a desired number of knots are arranged extracorporeally and the knots are then oriented toward the ASD so as to complement the suturing of the pericardium patch. The chest is closed as per normal with no drainage tube placement.

Another exemplary aspect of the present invention is directed to a method of providing a surgical device for closure of ASD with minimally invasive approach.

The method includes drawing a pericardial patch over a distal jaw of the surgical device, while keeping a first suture-guide channels attached to said distal jaw and a second suture-guide channels attached to a proximal jaw of the surgical device closed, inserting the surgical device through a hole incised in an intercostal space of a patient and drawing the surgical device toward the ASD, while keeping the proximal jaw of the surgical device extracorporeal, manipulating forward a guide rod of the surgical device to drive the distal jaw to negotiate the distal jaw through the ASD, opening the first suture-guide channels and the second suture-guide channels to position the first suture-guide channels and the second suture-guide channels around the ASD, withdrawing the distal jaw such that the distal jaw latches onto the proximal jaw, pulling back the pericardial patch in conjunction with an ASD rim to secure the pericardial patch and the ASD rim between the first suture-guide channels and the second suture-guide channels, employing a malleable needle extracorporeally to pass a suture thread into a space between the guide rod and an internal part of a cylindrical base, which supports a body portion of the surgical device, to suture the pericardial patch onto the ASD rim through the first suture-guide channels and the second suture-guide channels, re-steering forward the distal jaw to release the pericardial patch and to suture the pericardial patch onto the ASD rim, shutting the first suture-guide channels and the second suture-guide channels into respective original positions on the distal jaw and the proximal jaw, withdrawing the distal jaw from the ASD and lodging the distal jaw upon the proximal jaw, removing the surgical device from a body of the patient, and orienting a plurality of knots extracorporeally toward the ASD to complement said suture of the pericardial patch.

The method may further include driving the distal jaw away from the proximal jaw by a lever such that the distal jaw and the proximal jaw are spaced on different sides of an ASD hole, and after the suture thread sutures the pericardium patch, pulling the distal jaw backward toward the proximal jaw by the lever such that the first suture-guide channels couple with the second suture-guide channels to form a circle.

The device and method of the present invention enables that the minimally invasive closure of atrial septal defect procedure be performed in the operating room with CPB facilities available for any exigencies. This approach also minimizes the risk of atrioventricular valve distortion and obstruction of the superior and inferior venae cavae or coronary sinus.

While the invention has been described in terms of one or more embodiments, those skilled in the art will recognize that the invention can be practiced with modification within the spirit and scope of the appended claims. Specifically, one of ordinary skill in the art will understand that the drawings herein are meant to be illustrative, and the design of the inventive assembly is not limited to that disclosed herein but may be modified within the spirit and scope of the present invention.

Further, Applicants' intent is to encompass the equivalents of all claim elements, and no amendment to any claim the present application should be construed as a disclaimer of any interest in or right to an equivalent of any element or feature of the amended claim.

What is claimed is:

1. A surgical device for closure Atrial Septal Defect (ASD) with minimally invasive approach, said device comprising:
    a head portion which is movable and comprises:
        a distal jaw being distal relative to a person holding the surgical device;

a guide rod which drives the distal jaw; and
a plurality of first suture-guide channels attached to said distal jaw; and
a body portion which is stationary and comprises:
a cylindrical base;
a proximal jaw attached to said cylindrical base; and
a plurality of second suture-guide channels attached to said proximal jaw,
wherein the guide rod drives the distal jaw to pass a pericardium patch through a patient's ASD while the proximal jaw remains extracorporeal, and
wherein the first suture-guide channels and the second suture-guide channels guide a suture thread to suture the pericardium patch onto an ASD rim,
wherein said each of the first suture-guide channels is spaced apart from an adjacent one of the first suture-guide channels such that an arm of said each of the first suture-guide channels is oriented at a predetermined angle with respect to an arm of said adjacent one of the first suture-guide channels,
wherein each of the second suture-guide channels comprises an arm which connects a center portion of each of the second suture-guide channels to the proximal jaw,
wherein said each of the second suture-guide channels is spaced apart from an adjacent one of the second suture-guide channels such that the arm of said each of the second suture-guide channels is oriented at the predetermined angle with respect to an arm of said adjacent one of the second suture-guide channels,
wherein the first suture-guide channels is oriented at the predetermined angle to the second suture-guide channels such that the first suture-guide channels couple with the second suture-guide channels,
wherein the pericardium patch is connected to a suction device via a flexible pipe, and
wherein a threading thread attaches the pericardium patch to the distal jaw, ends of said threading thread being extracorporeal.

2. The surgical device of claim 1, wherein each of the first suture-guide channels comprises an arm which connects a center portion of each of the first suture-guide channels to the distal jaw.

3. The surgical device of claim 2, wherein the predetermined angle is 90 degrees.

4. The surgical device of claim 3, wherein the head portion comprises four of said first suture-guide channels.

5. The surgical device of claim 4, wherein the body portion comprises four of said second suture-guide channels.

6. The surgical device of claim 3, wherein the first suture-guide channels and the second suture-guide channels guide a needle that carries the suture thread to suture the pericardium patch onto the ASD rim.

7. The surgical device of claim 6, wherein the needle comprises a needle, and
wherein the needle passes the suture thread through a space between the guide rod and an internal section of the cylindrical base.

8. The surgical device of claim 3, wherein the pericardium patch is glued to said distal jaw.

9. A surgical device for closure Atrial Septal Defect (ASD) with minimally invasive approach, said device comprising:
a head portion which is movable and comprises:
a distal jaw being distal relative to a person holding the surgical device;
a guide rod which drives the distal jaw; and
four first suture-guide channels attached to said distal jaw;
a body portion which is stationary and comprises:
a cylindrical base;
a proximal jaw attached to said cylindrical base; and
four second suture-guide channels attached to said proximal jaw; and
a pericardium patch attached to the distal jaw, the pericardium patch being connected to a suction device via a flexible pipe,
wherein the guide rod drives the distal jaw to pass the pericardium patch through a patient's ASD while the proximal jaw remains extracorporeal, said pericardium patch being glued to said distal jaw,
wherein the first suture-guide channels and the second suture-guide channels guide a needle that carries a suture thread to suture the pericardium patch onto an ASD rim, said needle passing the suture thread through a space between the guide rod and an internal section of the cylindrical base,
wherein the first suture-guide channels are attached to a plurality of first arms, each of said first arms connecting a center portion of each of the first suture-guide channels to the distal jaw, said first arms being oriented at first predetermined angles with respect to a center of the guide rod,
wherein the second suture-guide channels are attached to a plurality of second arms, each of said second arms connecting a center portion of each of the second suture-guide channels to the proximal jaw, said second arms being oriented at second predetermined angles with respect to the center of the guide rod,
wherein a threading thread attaches the pericardium patch to the distal jaw, ends of said threading thread being extracorporeal,
wherein a lever drives the distal jaw away from the proximal jaw such that the distal jaw and the proximal jaw are spaced on different sides of an ASD hole, and
wherein after the suture thread sutures the pericardium patch, the lever pulls the distal jaw backward toward the proximal jaw such that the first suture-guide channels couple with the second suture-guide channels.

10. The surgical device of claim 9, wherein the first predetermined angles are 0 degree, 90 degrees, 180 degrees, and 270 degrees.

11. The surgical device of claim 10, wherein the second predetermined angles are 45 degrees, 135 degrees, 225 degrees, and 315 degrees.

* * * * *